United States Patent
Taguchi et al.

(10) Patent No.: US 8,652,411 B2
(45) Date of Patent: Feb. 18, 2014

(54) DEVICE FOR GENERATING CHLORINE DIOXIDE

(75) Inventors: Kazuhiko Taguchi, Osaka (JP); Shigeo Asada, Osaka (JP); Koichi Nakahara, Osaka (JP)

(73) Assignee: Taiko Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 13/635,819

(22) PCT Filed: Mar. 15, 2011

(86) PCT No.: PCT/JP2011/056030
§ 371 (c)(1),
(2), (4) Date: Oct. 17, 2012

(87) PCT Pub. No.: WO2011/118447
PCT Pub. Date: Sep. 29, 2011

(65) Prior Publication Data
US 2013/0034473 A1     Feb. 7, 2013

(30) Foreign Application Priority Data
Mar. 26, 2010  (JP) .................................. 2010-073841

(51) Int. Cl.
*B01J 19/08*    (2006.01)
(52) U.S. Cl.
USPC ....................................................... 422/186.3
(58) Field of Classification Search
USPC ....................................................... 422/186.3
See application file for complete search history.

(56) References Cited

U.S. PATENT DOCUMENTS 4,874,489 A * 10/1989 Callerame ................ 204/157.44
7,695,692 B2 * 4/2010 Sanderson ................... 422/186.3

FOREIGN PATENT DOCUMENTS

| JP | 61-48404 A | 3/1986 |
| JP | 64-71804 A | 3/1989 |
| JP | 4-300201 A | 10/1992 |
| JP | 2005-224386 A | 8/2005 |
| JP | 2005-263514 A | 9/2005 |
| JP | 2009-234887 A | 10/2009 |
| WO | 2007/094345 A1 | 8/2007 |

OTHER PUBLICATIONS

International Search Report w/translation from PCT/JP2011/056030 mailed May 17, 2011 (4 pages).

* cited by examiner

*Primary Examiner* — Kishor Mayekar
(74) *Attorney, Agent, or Firm* — Osha Liang LLP (57) ABSTRACT

A device for generating chlorine dioxide includes a cartridge having a chemical-holding space, in which a granular chlorite is held, a fan, and ultraviolet LED lamps disposed within a device main body, which can be separated into two or more detachable portions. The cartridge has light-transmitting properties and has a structure, which enables air to pass through the chemical-holding space and the inside of the device main body. When the fan is in operation, air is discharged from the inside of the device main body and, simultaneously therewith, air comes in from the outside of the device main body. By the action of ultraviolet rays, chlorine dioxide gas is generated from the chlorite present in the cartridge. By the operation of the fan, the gas is discharged from the inside of the device main body through air discharge ports.

20 Claims, 5 Drawing Sheets

DEVICE FOR GENERATING CHLORINE DIOXIDE

CROSS REFERENCE TO RELATED APPLICATIONS

This is a national stage application based on PCT/JP2011/056030, filed on Mar. 15, 2011, which claims priority to Japanese Patent Application No. JP2010-073841, filed on Mar. 26, 2010. This application claims the priority of these prior applications and incorporates their disclosures by reference in their entireties.

TECHNICAL FIELD

The present invention relates to a device for generating chlorine dioxide (hereinafter simply referred to as a "generating device"). More specifically, the present invention relates to a generating device utilizing a mechanism in which a solid chlorite is irradiated with ultraviolet rays to generate chlorine dioxide, and in particular, to a small-sized device for generating chlorine dioxide which is preferably mounted in an automobile (for example, a private car, a bus, or a taxi) or any other vehicle (for example, an airplane, a train, or a ship).

BACKGROUND ART

Devices for generating chlorine dioxide have been known which utilize the mechanism in which a solid chlorite is irradiated with ultraviolet rays to generate chlorine dioxide (see, for example, Patent Literature 1).

CITATION LIST

Patent Literature

Patent Literature 1: Japanese Patent Laid-Open No. 2005-224386

SUMMARY OF THE INVENTION

Technical Problem

However, many of the conventional devices for generating chlorine dioxide are not developed to be portable and are massive. Furthermore, the conventional devices use, as a main component (a chlorine dioxide source), a liquid containing a chlorite, or a gelled substance containing the liquid. If an attempt is made to carry the devices, the main component or a waste liquid may disadvantageously spill out. Moreover, even if the devices are simply miniaturized so as to be portable, a new problem results from the miniaturization of the devices, that is, the generation of chlorine dioxide lasts insufficiently (due to an insufficiency of the absolute amount of chlorite). This makes the continuous use of the devices difficult.

The present invention has been developed in view of the above-described circumstances. An object of the present invention is to provide a device for generating chlorine dioxide which has been miniaturized so that a chlorine dioxide source can be carried and which has no fear of liquid leakage and can be continuously used.

Solution to Problem

To accomplish the above object, a device for generating chlorine dioxide according to the present invention has the following configuration.

That is, the device according to the present invention is that for generating chlorine dioxide, characterized in that the device internally comprises an ultraviolet irradiation section that generates ultraviolet rays and a cartridge, the device comprises an air supply and discharge section in an outer wall thereof so that air can pass between an inside and an outside of the device, the cartridge internally comprises a chemical containing a solid chlorite, the cartridge is configured to allow air present outside the cartridge to contact the chemical present inside the cartridge, the cartridge is configured to allow the ultraviolet rays to pass through in such a manner that the chemical present inside the cartridge is irradiated with the ultraviolet rays generated by the ultraviolet irradiation section, and the chemical present inside the cartridge is irradiated with the ultraviolet rays to generate chlorine dioxide gas, and the chlorine dioxide gas is discharged to the outside of the device through the air supply and discharge section.

In the above configuration, when ultraviolet rays generated by the ultraviolet irradiation section hit the chlorite in the chemical inside the ultraviolet ray transmitting cartridge, chlorine dioxide gas is generated from the chlorite in the chemical, with moisture (water vapors) included in the air contributing to the reaction. The cartridge is configured to allow air to flow through so that the air present outside the cartridge and inside the device main body can contact the chemical present inside the cartridge. Thus, the chlorine dioxide gas generated in the cartridge flows from the cartridge into the device main body. The chlorine dioxide gas inside the device main body is further discharged to the outside of the device main body through the air supply and discharge port.

Furthermore, the above configuration allows chlorine dioxide gas to be generated from the solid chemical without generating a liquid substance as a byproduct. The device thus has no fear of liquid leakage.

In an embodiment of the device for generating chlorine dioxide according to the present invention, the device further internally includes a fan or an air pump, and the fan or the air pump is operated to enable the promotion of exchange of air between the outside and inside of the device through the air supply and discharge port. This configuration promotes the exchange of the air between the outside and inside of the device to allow the outside air, which generally contains more water vapors, to be fed into the device main body. Thus, the humidity (relative humidity) inside the device main body is raised so as to increase the frequency at which the chemical containing the solid chlorite contacts the moisture (water vapors). As a result, chlorine dioxide is likely to be generated from the solid chlorite irradiated with ultraviolet rays.

In an embodiment of the device for generating chlorine dioxide according to the present invention, the chemical containing the solid chlorite may contain a powdery or granule inorganic substance. Furthermore, in this case, the inorganic substance may be a porous inorganic substance and/or a deliquescent inorganic substance.

If a porous inorganic substance is used, the substance may be selected from a group consisting of, for example, zeolite, sepiolite, silica gel, bentonite, and apatite, as well as a calcined aggregate. The porous inorganic substance (internally having a countless number of pores) exerts the following effects. That is, part of the generated chlorine dioxide gas is absorbed (adsorbed) by the porous substance, which subsequently gradually discharges chlorine dioxide gas (controlled release). Thus, even when a power source is turned off (switched off) to stop the ultraviolet irradiation, chlorine dioxide is continuously discharged for a while, and effects of the chlorine dioxide can be prolonged. In contrast, if a nonporous inorganic substance is used, when the power source is turned off (switched off) to stop the ultraviolet irradiation, the generation of chlorine dioxide can also be stopped.

If a deliquescent inorganic substance is used, the substance may be selected from a group consisting of, for example, calcium chloride, magnesium chloride, and aluminum chloride. In this case, moisture present in the ambient air can be actively taken in to increase the ambient humidity of the chlorite (solid). Thus, chlorine dioxide gas is expected to be efficiently and stably generated.

In an embodiment of the device for generating chlorine dioxide according to the present invention, in the chemical containing the solid chlorite, a content of the chlorite can be 0.1 wt % to 50 wt % of the whole chemical. This configuration enables the concentration (level of concentration) of the solid chlorite to be suppressed, allowing possible danger to be avoided. Furthermore, the chemical is very unlikely to be fired because it is surrounded by the inorganic substance.

In an embodiment of the device for generating chlorine dioxide according to the present invention, the chemical containing the solid chlorite may further contain alkali hydroxide.

In an embodiment of the device for generating chlorine dioxide according to the present invention, the device may be configured to be openable and closable so as to allow the cartridge itself or the chemical inside the cartridge to be changed. This configuration allows a new chemical to be introduced without the need to dispose of the device itself, thus allowing chlorine dioxide to be continuously generated. Therefore, the device is excellent both in ecology and in economy.

In an embodiment of the device for generating chlorine dioxide according to the present invention, the device can be mounted and used in a vehicle. Then, in a small space in the vehicle or the like, possible infection can be prevented, or a smell of tobacco or a smell of food can be prevented from drifting. Of course, the device can not only be mounted in a vehicle, but also be used in a living room or a bathroom, for example.

DESCRIPTION OF EMBODIMENTS

Chlorite

Examples of chlorite for use in the present invention include an alkaline metal chlorite salt or an alkaline earth metal chlorite salt. Examples of the alkaline metal chlorite salt include sodium chlorite, potassium chlorite, or lithium chlorite. Examples of the alkaline earth metal chlorite salt include calcium chlorite, magnesium chlorite, or barium chlorite. In particular, the sodium chlorite or the potassium chlorite is preferable due to the ease of availability thereof, and the sodium chlorite is most preferable. One type of these chlorites may be independently used, or two or more types of these chlorites may be used together.

A chemical containing a solid chlorite which is used for the present invention refers to a chemical containing chlorite in a solid state. As such a solid chlorite, a powdery or granular chlorite may be directly used. Alternatively, a powdery or granular chlorite may be used by mixing the powdery or granular chlorite with an appropriate inorganic substance carrier. Moreover, a solid chlorite may be obtained by mixing a water solution of chlorite with an appropriate inorganic substance carrier and drying the resultant solution as necessary.

Furthermore, the chemical containing the solid chlorite which is used for the present invention may further contain alkali hydroxide. The addition of the alkali hydroxide enables the pH of the chemical to be adjusted, thus improving the stability of the chemical itself and suppressing wasteful discharge of chlorine dioxide gas during storage or the like when the chemical is not irradiated with ultraviolet rays.

For example, if a solid chlorite is used which is obtained by mixing a water solution of chlorite with an appropriate inorganic substance carrier and drying the resultant solution as necessary, the above-described alkali hydroxide may be mixed with the water solution of chlorite. Other methods may be used to add the alkali hydroxide.

Examples of such alkali hydroxide include lithium hydroxide, sodium hydroxide, or potassium hydroxide. In particular, the sodium hydroxide or the potassium hydroxide is preferable due to the ease of availability thereof, and the sodium hydroxide is most preferable. One type of these alkali hydroxides may be independently used, or two or more types of these alkali hydroxides may be used together.

In the specification, the size of the powder or granule may be roughly indicated as follows. For example, the powder refers to a solid of (average) particle size 0.01 mm to 1 mm. The granule refers to a solid of (average) particle size 1 mm to 30 mm. However, the size of the powder or granule is not particularly limited. In view of ease in handling, the powder or granule is preferably a solid of (average) particle size 1 mm to 10 mm.

Ultraviolet Light Emitter

Any conventional ultraviolet light emitter may be used for the present invention provided that the ultraviolet light emitter emits only ultraviolet rays or light containing ultraviolet rays. Thus, the wavelength of the light emitter as used herein is not limited to an ultraviolet wavelength (near ultraviolet rays of wavelength 380 nm to 200 nm, far ultraviolet rays of wavelength 200 nm to 10 nm, or extreme ultraviolet rays of wavelength 1 nm to 10 nm). The ultraviolet rays may include visible light of wavelength 720 nm to 380 nm. The ultraviolet light emitter may be, for example, polyolefin mixed with calcium sulfide or barium sulfide, or any of various synthetic resin materials such as polyester. Alternatively, a black light or an ultraviolet LED (Light Emitting Diode) lamp may be used as an ultraviolet light emitter according to the present invention. In particular, a small-sized lamp may be used, and an ultraviolet LED lamp is preferably used due to its long life.

A wavelength of at most 280 nm is likely to be absorbed by the atmosphere. A wavelength of 280 nm to 320 nm is likely to be absorbed by glass or resin. Thus, in view of the generation efficiency of chlorine dioxide gas, light containing many ultraviolet rays of wavelength 320 nm to 380 nm is preferred.

However, the present invention does not particularly intend to limit the ultraviolet rays to such wavelengths.

Inorganic Substance

Examples of the powdery or granular inorganic substance for use in the present invention include zeolite, sepiolite, silica gel, bentonite, and apatite, as well as a calcined aggregate and metal such as aluminum and copper. If the inorganic substance is a porous substance such as sepiolite, montmorillonite, diatomaceous earth, talc, or zeolite, the inorganic substance is effective for temporarily taking in chlorine dioxide gas generated from chlorite to control the amount of chlorine dioxide gas discharged, thus extending the duration for which chlorine dioxide gas is generated. The calcined aggregate can be used which may be obtained by calcining one or two or more types of materials selected from a group consisting of an animal bone (the animals include mammals, fish, and birds), a seashell, and coral. In particular, the calcined aggregate, which is obtained by calcining an animal bone, notably a bone of a grass eating animal such as a cow, a horse, or a sheep, is preferably used.

Furthermore, the powdery or granular inorganic substance for use in the present invention may be, for example, a deliquescent substance such as calcium chloride, magnesium chloride, or aluminum chloride. These deliquescent substances are capable of actively taking in moisture present in the ambient air, thus increasing the ambient humidity of the chlorite (solid). As a result, chlorine dioxide gas can be efficiently and stably generated.

Furthermore, of course, a plurality of inorganic substances as described above can be simultaneously used. For example, the porous substance and the deliquescent substance can of course be used together.

If the inorganic substance is allowed to coexist with the solid chlorite, its blending ratio is not particularly limited but the amount of the chlorite is preferably 0.1 wt % to 50 wt % (of the whole chemical) in order to reduce the concentration of the chlorite to avoid possible danger. Furthermore, if the deliquescent substance is used as the inorganic substance, the content rate of the deliquescent substance is preferably approximately 0.1 wt % to 30 wt % (of the whole chemical).

Humidity

In view of the generation efficiency of chlorine dioxide, in general, the higher the ambient humidity of the powdery or granular chlorite is, the better the efficiency is. However, it is considered that if water is condensed, it may affect an electric system. Thus, the relative humidity inside the device main body is preferably between 20% and 99%. If the above-described inorganic substance is a deliquescent substance such as calcium chloride, magnesium chloride, and aluminum chloride, the inorganic substance can actively take in the moisture present in the ambient air to increase the ambient humidity of the chlorite. Thus, chlorine dioxide gas can be efficiently and stably generated. Alternatively, an air pump (blower) may be used as means for actively feeding water vapor-containing air from the outside of the device to the inside of the device in order to increase the frequency at which the solid chlorite contacts the water vapors. Furthermore, if a fan is used inside the device, operation of the fan also promotes the exchange of the inside air and the outside air. Moreover, a Peltier element (Peltier effect) may be utilized which condenses and collects the moisture in the air (the Peltier element may be subjected to water vapor infiltration or dew condensation but this disadvantage may be utilized to raise the humidity).

Other

Other means may be taken as follows.

(1) A hygrometer that measures the humidity inside the device main body may be provided so that with the amount of moisture monitored, the humidity can be controlled using the Peltier element.

(2) A gas sensor may be provided which measures the concentration of the chlorine dioxide inside the device main body, or the concentration of the chlorine dioxide discharged through the air discharge port. Thus, with the amount of generated chlorine dioxide monitored, the concentration of chlorine dioxide gas can be controlled by turning on and off the ultraviolet ray source.

(3) The chlorite and the inorganic substance, which is premixed and molded into a tablet instead of being handled separately, can be used.

(4) A device for stirring a chemical-holding space in the cartridge may be provided to stir up the solid chlorite in the cartridge. The purpose of the stir is to increase the efficiency with which the solid chlorite contacts the moisture (water vapors) in the air or to suppress a decrease in the amount of generated chlorine dioxide by changing a site where ultraviolet rays hit the chemical, since there is a tendency that the amount of generated chlorine dioxide decreases if the same site in the chemical is irradiated with ultraviolet rays for a long time. Alternatively, a method for stirring up the solid chlorite in the cartridge by vibrating the cartridge may be employed. As a method for vibrating the cartridge itself, for example, a device may be provided which regularly or irregularly rotates or moves the cartridge itself using a vibration device (vibrator) with a small-sized motor (a motor with an eccentric rotating shaft) or a motor (rotating device). Alternatively, a device may be provided which regularly turns the cartridge upside down inside the device main body.

The terms herein are used to describe particular embodiments and are not intended to limit the invention.

Furthermore, the term "include (or includes or including), contain (or contains or containing), or comprise (or comprises or comprising)" as used herein is intended to mean that a described item (a member, a step, an element, a number, or the like) is present unless the context clearly requires otherwise and not to exclude the presence of any other item(s) (a member, a step, an element, a number, or the like).

Unless otherwise defined, all the terms used herein (including technical and scientific terms) have the same meanings as those which are broadly understood by those skilled in the art to which the present invention belongs. The terms as used herein should be understood to have, unless otherwise defined, meanings consistent with the meanings in the specification and related technical fields, and should not be idealized or appreciated in an excessively formalized way.

The embodiments of the present invention may be described with reference to schematic diagrams. However, in order to make the descriptions clear, the schematic diagrams may be depicted exaggeratingly.

The present invention will be described below in further detail with reference to an embodiment. However, the present invention may be embodied in various aspects and should not be understood to be limited to the described embodiment.

Embodiment

<<Manufacture Embodiment 1>>

Figure 1:
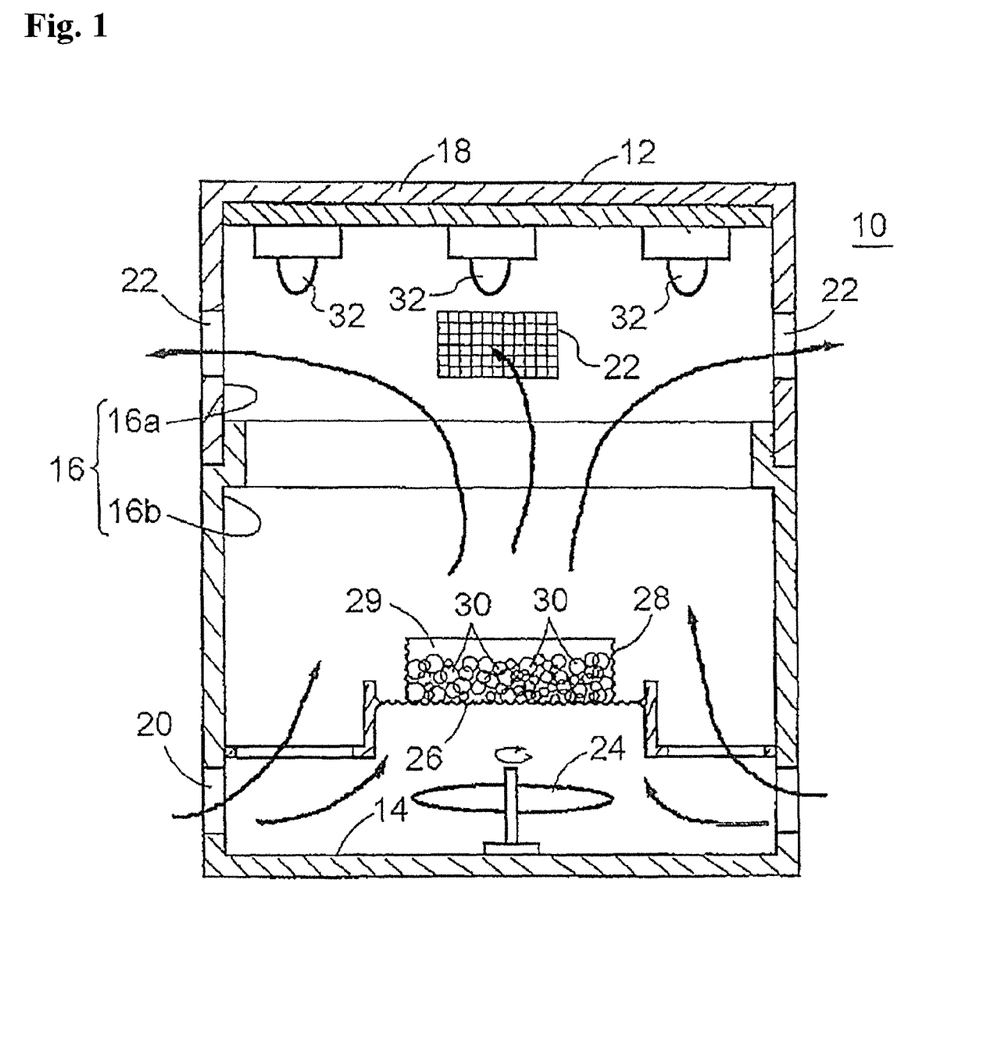
FIG. 1 is a partial vertical cross-sectional view of an on-board generating device 10 according to an embodiment of the present invention.

FIG. 1 is a vertical cross-sectional view of an on-board (small-sized) generating device 10 according to an embodiment of the present invention (FIG. 1 shows the internal structure of the device 10). The device was generally cylindrical and about 15 centimeters in height and 6.5 centimeters in radius. The device main body 12 of the generating device 10 includes a disk-like bottom plate portion 14, a cylindrical side wall portion 16 extending vertically from the bottom plate portion 14, and a disk-like cover plate portion 18 that closes the top of the side wall portion 16. The side wall portion 16 of the device main body 12 is divided at a position close to a central portion thereof in the vertical direction, into two portions, an upper side wall portion 16a and a lower side wall portion 16b. The upper side wall portion 16a and the lower side wall portion 16b are integrated together by detachably fitting a lower end of the upper side wall portion 16a over an upper end of the lower side wall portion 16b. That is, the device main body 12 can be separated into two detachable portions at the side wall portion 16.

Furthermore, the side wall portion 16 includes air supply and discharge ports 20 formed in the lower side wall portion 16b at predetermined intervals in a circumferential direction thereof and allowing air to pass through between the outside and inside of the device main body 12. The side wall portion 16 also include air supply and discharge ports 22 formed in the upper side wall portion 16a at predetermined intervals in the circumferential direction thereof and allowing air to pass through between the outside and inside of the device main body 12.

A fan 24 is provided in an inner bottom portion of the device main body 12 (in a central portion of the bottom plate portion 14 in a radial direction thereof). The fan 24 is operated to generate a rising air current inside the device main body 12. Furthermore, a mount 26 formed of a net-like plate member such as a wire mesh is provided above the fan 24. A bottomed cylinder-like cartridge 28 with a top portion substantially open (for example, the top opening portion of the cartridge may be covered with a net-like plate member such as a wire mesh which includes openings) is placed on the mount 26. The inside of the cartridge 28 forms a chemical-holding space 29 in which a chemical 30 containing a solid chlorite is held. An example of the chemical is a mixture of a granular solid sodium chlorite of average particle size 3 mm to 5 mm (25 wt %), an inorganic substance such as a sepiolite (65 wt %), and calcium chloride (10 wt %). The cartridge 28 is formed of a net plate member not only in the top portion thereof but also in a side portion and a bottom portion thereof; the net plate member includes openings, each of which is sized so as to prevent a held object from falling through the openings. This secures the permeability of ultraviolet rays and also allows air to flow between the chemical-holding space 29 and the inside of the device main body 12. The cartridge 28 may be formed of a permeable material (permeable material of ultraviolet rays) such as a glass material or a synthetic resin material, instead of the net plate member. In this case, a plurality of pores may be formed in the cartridge 28 so that air can pass through between the chemical-holding space 29 and the inside of the device main body 12.

As an ultraviolet light emitter, a plurality of ultraviolet LED (Light Emitting Diode) lamps 32 are provided in an inner top portion of the device main body 12 (on a bottom surface of the cover plate portion 18) so as to emit ultraviolet rays of wavelength 320 nm to 380 nm downward (that is, toward the cartridge 28).

When a power source (not shown in the drawings) of the generating device 10 is turned on, the fan 24 is operated and the ultraviolet LED lamps 32 emit ultraviolet rays. When the emitted ultraviolet rays reach sodium chlorite in the cartridge 28 (the sodium chlorite in the cartridge 28 is irradiated with the ultraviolet rays), chlorine dioxide gas is gradually generated from the sodium chlorite, with the moisture (water vapors) in the air also contributing to the reaction. The chlorine dioxide gas is discharged from the inside of the cartridge 28 to the outside of the cartridge 28 (the inside of the device main body 12). The fan 24 is operated to discharge the air present inside the device main body 12 to the outside of the device main body 12 through the air supply and discharge ports 20 and 22 (particularly 22). The air present outside the device main body 12 also flows into the device main body 12 through the air supply and discharge ports 20 and 22 (particularly 20). Thus, it will be understood that such air flows as shown by arrows in FIG. 1 are expected to occur. In this manner, the chlorine dioxide gas present inside the device main body 12 is discharged to the outside of the device main body 12 and drifts around the device to exert the effects of chlorine dioxide, for example, an antiviral inactivation effect, an antibacterial effect, and a deodorization effect.

Figure 2:
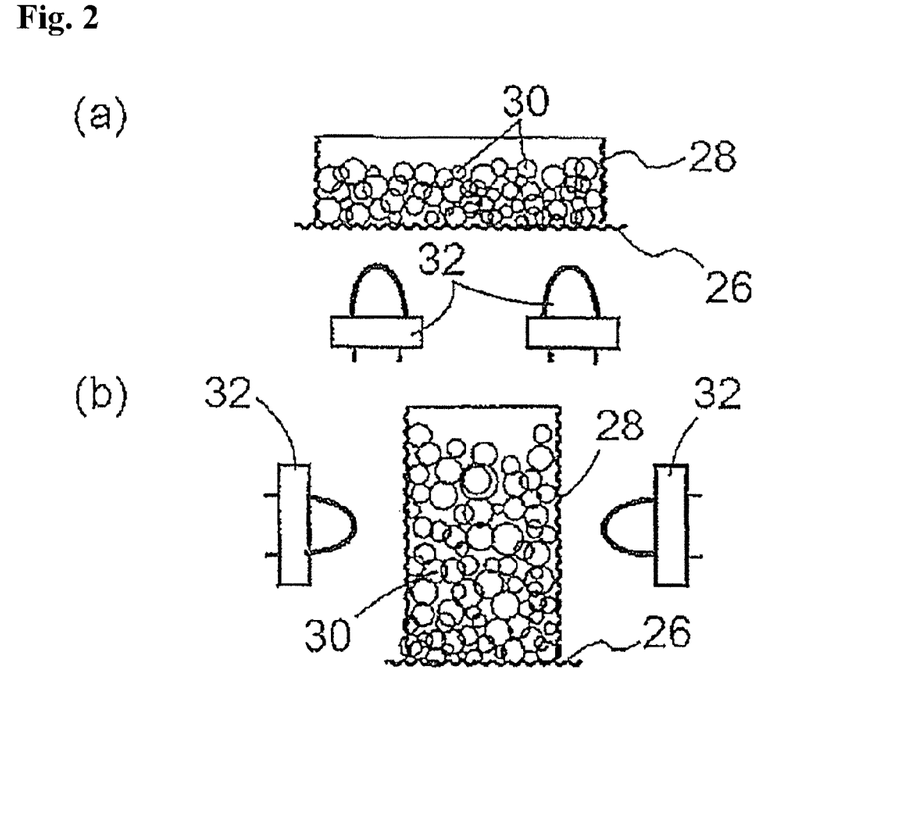
FIG. 2 is a schematic diagram showing the positional relationship between a cartridge 28 and ultraviolet LED lamps according to another embodiment of the present invention.

The positional relationship between the cartridge 28 and ultraviolet LED lamps 32 is not particularly limited. For example, as shown in FIG. 2(a), one or more ultraviolet LED lamps 32 may be arranged immediately below a bottom plate of the bottomed cylindrical cartridge 28 (the lamp main body of the ultraviolet LED lamp 32 and the bottom plate of the cartridge 28 may be arranged opposite each other). Alternatively, as shown in FIG. 2(b), particularly if the cartridge 28 is vertically long, the ultraviolet LED lamps 32 may be arranged outside of and immediately lateral to the cartridge 28.

Figure 3:
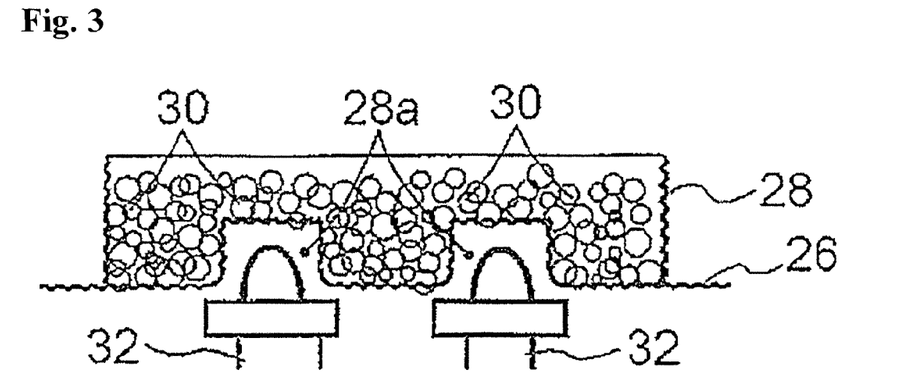
FIG. 3 is a schematic diagram showing the positional relationship between the cartridge 28 and the ultraviolet LED lamps according to yet another embodiment of the present invention.

Furthermore, the following configuration may be devised in order to allow ultraviolet rays emitted by the ultraviolet LED lamps 32 to efficiently reach the sodium chlorite inside the cartridge 28 so as to efficiently generate chlorine dioxide. That is, as shown in FIG. 3, the bottom plate of the bottomed cylindrical cartridge 28 may be formed to protrude upward (toward the inside of the cartridge 28) (the bottom plate may be recessed.) so as to provide one or more upward bulging dome-like lamp-holding spaces 28a. When the cartridge 28 is installed inside the device main body 12 (if the cartridge 28 is placed on the mount 26, the mount 26 is partly cut out or a hole is made in the mount 26), the lamp main body of the ultraviolet LED lamp 32 is held in each of the lamp-holding spaces 28a of the cartridge 28. This increases the rate of utilization of the emitted ultraviolet rays to improve the generation efficiency of chlorine dioxide from the sodium chlorite.

As described above, in addition to the solid chlorite, the inorganic substance is held inside the cartridge 28. If the inorganic substance is a porous substance such as sepiolite, at least part of the generated chlorine dioxide is, before being discharged to the outside of the cartridge 28, absorbed (adsorbed) by and accumulated in the inorganic substance, and then is discharged to the outside of the cartridge 28. Thus, the coexistence of the sodium chlorite and the porous inorganic substance allows chlorine dioxide to be continuously discharged. Even after the power source is turned off, the effects of chlorine dioxide can be obtained.

Furthermore, the cartridge 28 can be easily replaced with a new one, and the device main body 12 can be repeatedly used over and over again. That is, the power source for the generating device 10 is turned off, and the device main body 12 is separated into the upper side wall portion 16a and the lower side wall portion 16b. The used cartridge 28 is removed from the mount 26, and a new cartridge 28 (with a chemical containing a solid chlorite included therein) is placed on the mount 26. Again, the upper side wall portion 16a and the lower side wall portion 16b are fitted and thus are integrated together, and the power source is turned on. Thus, chlorine dioxide can be continuously generated. In this case, a solid chlorite that does not belong to Class 1 Hazardous Materials is used.

With reference to test examples, the effects of the present invention will be described below.

<<Text Example 1>>

One gram of 79 wt % powdery sodium chlorite was mixed with 0.5 ml of 1 N sodium hydroxide solution, and the mixture was subsequently dried. The mixture was then mixed with 4 g of powdery zeolite and 0.5 g of powdery calcium chloride. The resultant mixture was stirred up to obtain about 5.5 g of chemical for use in the tests. The concentration of sodium chlorite in the chemical was about 14 wt % (0.79/5.5× 100=14.36 wt %).

Figure 4:
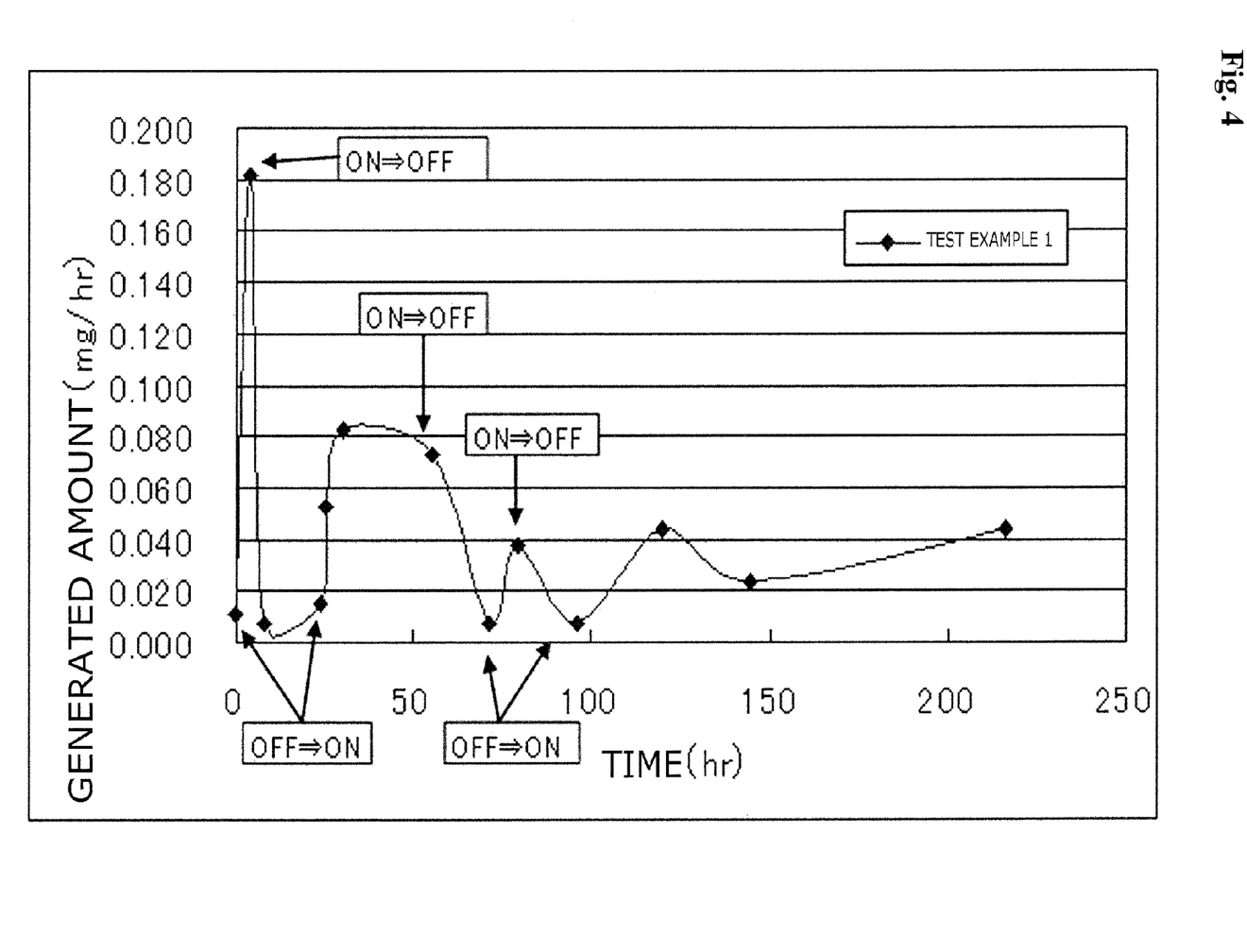
FIG. 4 is a diagram showing the results of tests using the device according to the present invention.

The whole quantity of the chemical was placed in the device in FIG. 1, and the power source for the device was turned on. While the fan attached to the device was in operation, the ultraviolet LEDs were turned on and off, and the amount of chlorine dioxide generated was measured. The measurement was carried out according to the following method. That is, the device in FIG. 1 containing the chemical was installed inside 6.5 L box prepared for measurement of the amount of chlorine dioxide generated. About 1 L/min of air was passed through the box, and the concentration of chlorine dioxide gas was measured using a gas detector tube 23 M (GASTEC CORPORATION). Furthermore, a flowmeter was used to measure the flow rate of the air flowing through the measuring box, and the amount of chlorine dioxide generated was calculated. The results are shown in Table 1 and FIG. 4.

TABLE 1

| Time (hr) | Operation (State) of Ultraviolet LEDs | Test Example 1 (mg/hr) |
|---|---|---|
| 0 | OFF→ON | 0.010 |
| 4 | ON→OFF | 0.181 |
| 8 | (OFF) | 0.007 |
| 24 | OFF→ON | 0.015 |
| 25 | (ON) | 0.052 |
| 30 | (ON) | 0.082 |
| 55 | ON→OFF | 0.073 |
| 71 | OFF→ON | 0.007 |
| 79 | ON→OFF | 0.037 |
| 96 | OFF→ON | 0.007 |
| 120 | (ON) | 0.044 |
| 144 | (ON) | 0.034 |
| 216 | (ON) | 0.044 |

<<Test Example 2>>

Figure 5:
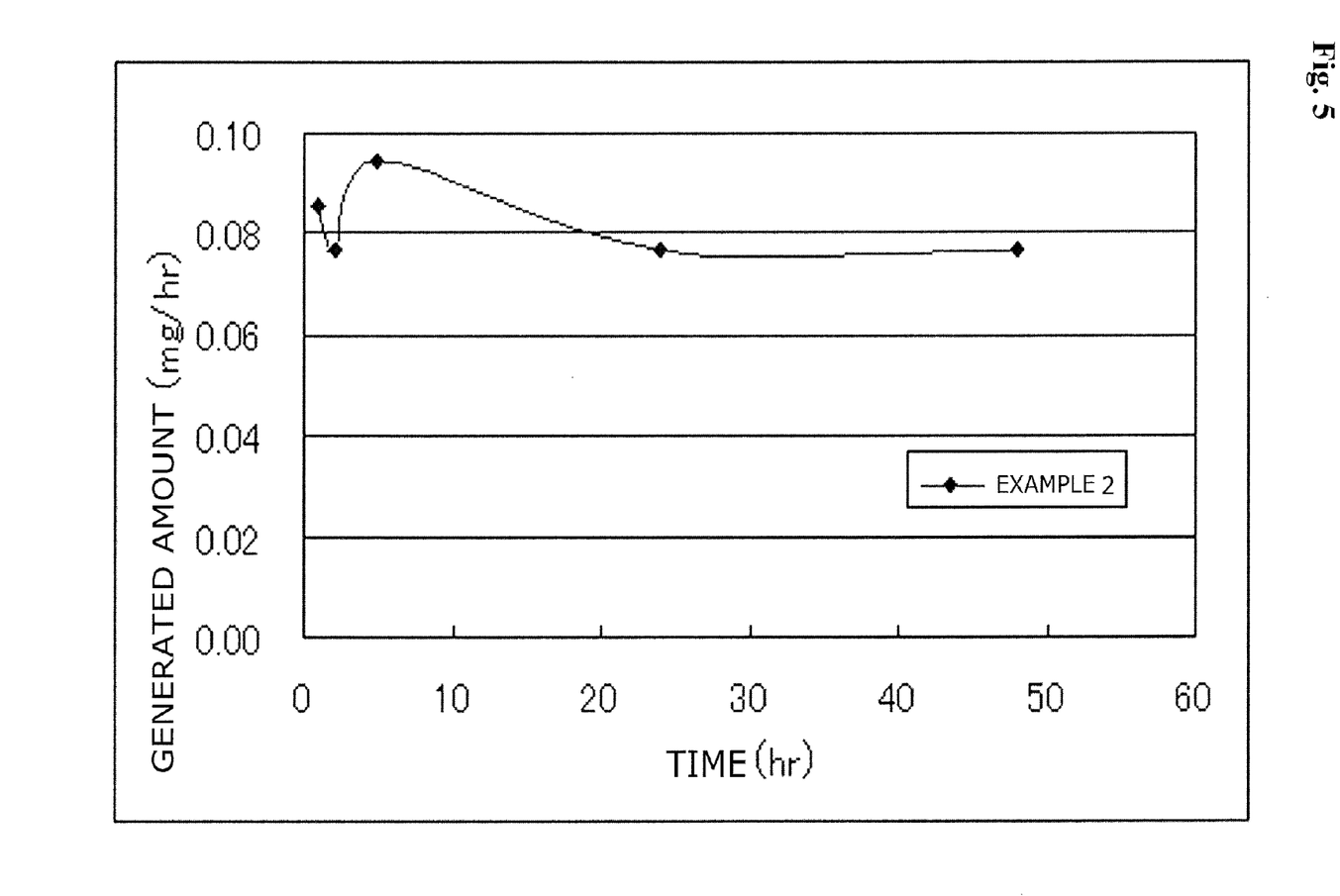
FIG. 5 is a diagram showing the results of tests using the device according to the present invention.

A spray was used to spray and adsorb 70 g of 25 wt % sodium chlorite solution to 100 g of calcined sepiolite, and the mixture was then dried. A chemical for use in the tests was thus obtained. The concentration of sodium chlorite in the chemical was measured by adding water to the chemical and using an ultrasonic cleaner to elute the sodium chlorite. The concentration of the sodium chlorite was determined by titration to be 11 wt %. 15 g of the chemical was used for the following tests. To determine the amount of chlorine dioxide generated from the chemical when the ultraviolet LEDs were turned off, the amount of chlorine dioxide generated was measured as is the case with Test Example 1. The results are shown in Table 2 and FIG. 5.

TABLE 2

| Ultraviolet LED State | Time (hr) | Test Example 2 (mg/hr) |
|---|---|---|
| OFF | 1 | 0.09 |
|  | 2 | 0.08 |
|  | 5 | 0.09 |
|  | 24 | 0.08 |
|  | 48 | 0.08 |

<<Test Example 3>>

Figure 6:
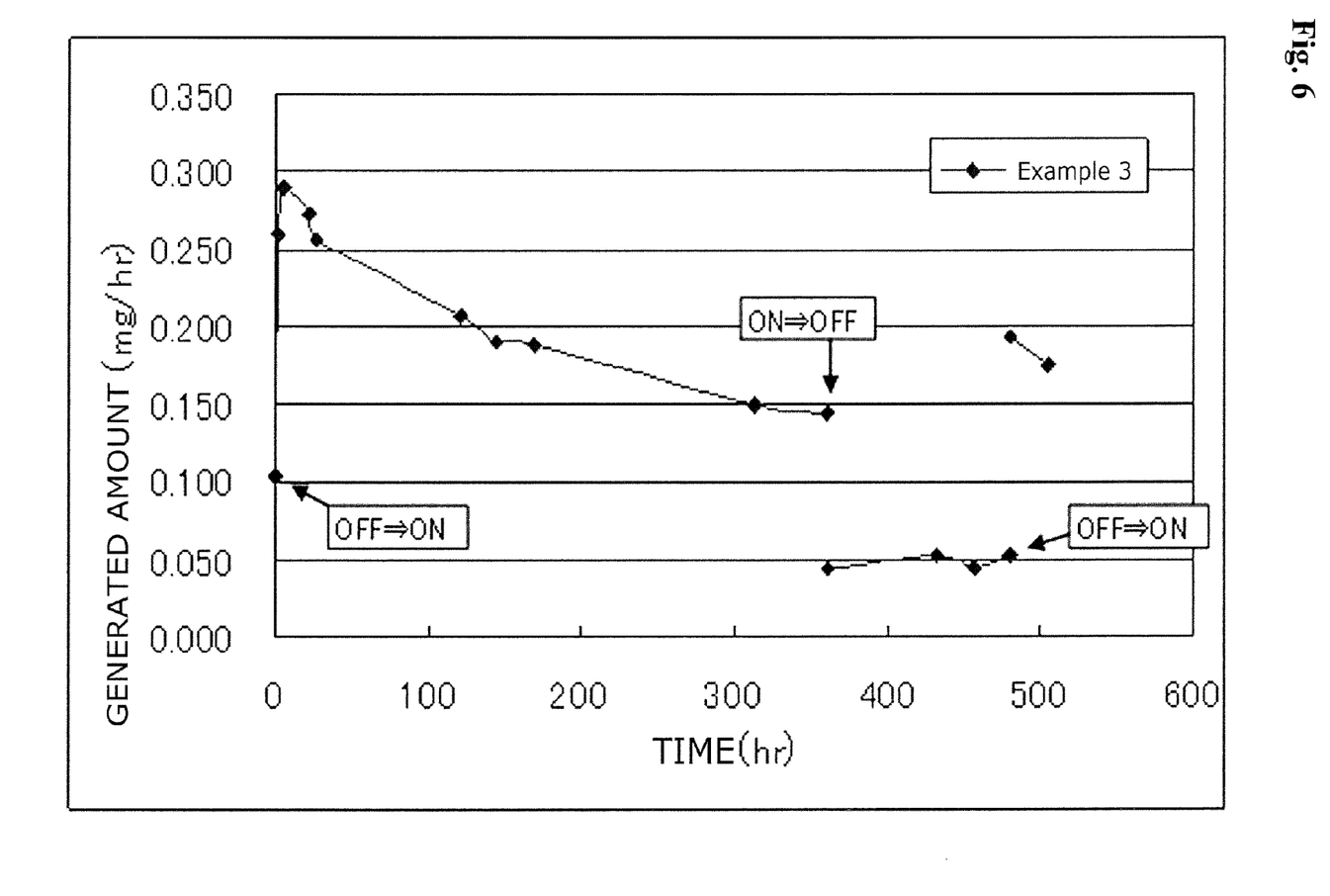
FIG. 6 is a diagram showing the results of tests using the device according to the present invention.

To determine the amount of chlorine dioxide generated from the same chemical when the ultraviolet LEDs were turned on and off, the amount of chlorine dioxide generated was measured as is the case with Test Examples 1 and 2, using 15 g of the chemical identical to that in Test Example 2. Specifically, 360 hours after the start of the measurement, the ultraviolet LEDs were switched from the on state to the off state. Furthermore, 456 hours after the start of the measurement, the ultraviolet LEDs were switched from the off state to the on state. The results are shown in Table 3 and FIG. 6.

TABLE 3

| Ultraviolet LED State | Time (hr) | Test Example 3 (mg/hr) |
|---|---|---|
| ON | 0 | 0.104 |
|  | 2 | 0.260 |
|  | 4 | 0.291 |
|  | 21 | 0.274 |
|  | 26 | 0.257 |
|  | 120 | 0.208 |
|  | 144 | 0.190 |
|  | 168 | 0.188 |
|  | 312 | 0.150 |
|  | 360 | 0.145 |
| OFF | 432 | 0.052 |
|  | 456 | 0.044 |
| ON | 480 | 0.194 |
|  | 504 | 0.175 |

As described above, in all the test examples, the amount of generated chlorine dioxide gas was increased during the irradiation by the ultraviolet LEDs. They show that all the results are favorable. Test Example 2 shows the result that no ultraviolet rays were irradiated by the ultraviolet LEDs. However, only a very low concentration of chlorine dioxide gas was occurred, and an increase in the amount of generated chlorine dioxide gas was not observed unlike in the case of the irradiation of the ultraviolet LEDs. This confirms that the amount of chlorine dioxide generated can be controlled by irradiating the solid chlorite with ultraviolet rays.

Industrial Applicability

The present invention is applicable to a small-sized device for generating chlorine dioxide which is preferably mounted in a vehicle such as an automobile (a private car, a bus, or a taxi), an airplane, a train, or a ship.

Reference Signs List

10 Generating device
12 Device main body
14 Bottom plate portion
16 Side wall portion
18 Cover plate portion
20 Air supply and discharge port
22 Air supply and discharge port
24 Fan
26 Mount
28 Cartridge
29 Chemical-holding space
32 Ultraviolet LED lamp

The invention claimed is:

1. A device for generating chlorine dioxide, characterized in that
the device internally comprises an ultraviolet irradiation section that generates ultraviolet rays and a cartridge;
the device comprises an air supply and discharge section in an outer wall thereof so that air can pass between an inside and an outside of the device;
the cartridge internally comprises a chemical comprising a solid chlorite;

the cartridge is configured to allow air present outside the cartridge to contact the chemical present inside the cartridge;

the cartridge is configured to allow the ultraviolet rays to pass through in such a manner that the chemical present inside the cartridge is irradiated with the ultraviolet rays generated by the ultraviolet irradiation section; and the chemical present inside the cartridge is irradiated with the ultraviolet rays to generate chlorine dioxide gas, and the chlorine dioxide gas is discharged to the outside of the device through the air supply and discharge section.

2. The device for generating chlorine dioxide according to claim 1, characterized in that the device internally comprises a fan or an air pump; and the fan or the air pump is operated to promote exchange of air between the outside and inside of the device.

3. The device for generating chlorine dioxide according to claim 2, characterized in that the chemical containing the solid chlorite comprises a powdery or granule inorganic substance.

4. The device for generating chlorine dioxide according to claim 2, characterized in that the device is openable and closable so as to allow the cartridge itself or the chemical inside the cartridge to be changed.

5. The device for generating chlorine dioxide according to claim 2, characterized in that the device is mounted in a vehicle.

6. The device for generating chlorine dioxide according to claim 1, characterized in that the chemical containing the solid chlorite comprises a powdery or granule inorganic substance.

7. The device for generating chlorine dioxide according to claim 6, characterized in that in the chemical containing the solid chlorite, a content of the chlorite is 0.1 wt % to 50 wt % of the whole chemical.

8. The device for generating chlorine dioxide according to claim 7, characterized in that the inorganic substance is a porous inorganic substance and/or a deliquescent inorganic substance.

9. The device for generating chlorine dioxide according to claim 7, characterized in that the device is openable and closable so as to allow the cartridge itself or the chemical inside the cartridge to be changed.

10. The device for generating chlorine dioxide according to claim 7, characterized in that the device is mounted in a vehicle.

11. The device for generating chlorine dioxide according to claim 6, characterized in that the inorganic substance is a porous inorganic substance and/or a deliquescent inorganic substance.

12. The device for generating chlorine dioxide according to claim 11, characterized in that the porous inorganic substance is selected from a group consisting of zeolite, sepiolite, silica gel, bentonite, and apatite, as well as a calcined aggregate, and the deliquescent inorganic substance is selected from a group consisting of calcium chloride, magnesium chloride, and aluminum chloride.

13. The device for generating chlorine dioxide according to claim 12, characterized in that the device is openable and closable so as to allow the cartridge itself or the chemical inside the cartridge to be changed.

14. The device for generating chlorine dioxide according to claim 11, characterized in that the device is openable and closable so as to allow the cartridge itself or the chemical inside the cartridge to be changed.

15. The device for generating chlorine dioxide according to claim 6, characterized in that the chemical further comprises alkali hydroxide.

16. The device for generating chlorine dioxide according to claim 15, characterized in that the device is openable and closable so as to allow the cartridge itself or the chemical inside the cartridge to be changed.

17. The device for generating chlorine dioxide according to claim 6, characterized in that the device is openable and closable so as to allow the cartridge itself or the chemical inside the cartridge to be changed.

18. The device for generating chlorine dioxide according to claim 6, characterized in that the device is mounted in a vehicle.

19. The device for generating chlorine dioxide according to claim 1, characterized in that the device is openable and closable so as to allow the cartridge itself or the chemical inside the cartridge to be changed.

20. The device for generating chlorine dioxide according to claim 1, characterized in that the device is mounted in a vehicle.

* * * * *